US012689063B2

(12) United States Patent
Kim et al.

(10) Patent No.: US 12,689,063 B2
(45) Date of Patent: Jul. 21, 2026

(54) LITHIUM SECONDARY BATTERY

(71) Applicant: LG Energy Solution, Ltd., Seoul (KR)

(72) Inventors: Ha Eun Kim, Daejeon (KR); Chul Haeng Lee, Daejeon (KR); Jeong Woo Oh, Daejeon (KR); Byung Chun Park, Daejeon (KR); Hyung Tae Kim, Daejeon (KR); Young Mi Seo, Daejeon (KR)

(73) Assignee: LG Energy Solution, Ltd., Seoul (KR)

( * ) Notice: Subject to any disclaimer, the term of this patent is extended or adjusted under 35 U.S.C. 154(b) by 413 days.

(21) Appl. No.: 18/275,110

(22) PCT Filed: Oct. 4, 2022

(86) PCT No.: PCT/KR2022/014922

§ 371 (c)(1),
(2) Date: Jul. 31, 2023

(87) PCT Pub. No.: WO2023/059037

PCT Pub. Date: Apr. 13, 2023

(65) Prior Publication Data

US 2024/0154166 A1 May 9, 2024

(30) Foreign Application Priority Data

Oct. 7, 2021 (KR) ........................ 10-2021-0133482
Sep. 30, 2022 (KR) ........................ 10-2022-0125821

(51) Int. Cl.

| | |
|---|---|
| ***H01M 10/0567*** | (2010.01) |
| ***C07D 233/58*** | (2006.01) |
| ***H01M 4/505*** | (2010.01) |
| ***H01M 4/525*** | (2010.01) |
| ***H01M 10/0525*** | (2010.01) |
| ***H01M 10/0568*** | (2010.01) |
| *H01M 4/02* | (2006.01) |

(52) U.S. Cl.

CPC ...... *H01M 10/0567* (2013.01); *C07D 233/58* (2013.01); *H01M 4/505* (2013.01); *H01M 4/525* (2013.01); *H01M 10/0525* (2013.01); *H01M 10/0568* (2013.01); *H01M 2004/028* (2013.01); *H01M 2300/0037* (2013.01)

(58) Field of Classification Search

None

See application file for complete search history.

(56) References Cited

U.S. PATENT DOCUMENTS

| | | | |
|---|---|---|---|
| 2003/0165733 | A1 | 9/2003 | Takehara et al. |
| 2006/0068282 | A1 | 3/2006 | Kishi et al. |
| 2007/0191612 | A1 | 8/2007 | Ohno et al. |
| 2017/0237122 | A1 | 8/2017 | Lee et al. |
| 2020/0373616 | A1 | 11/2020 | Choi et al. |
| 2021/0234200 | A1 | 7/2021 | Kim et al. |
| 2022/0223911 | A1 | 7/2022 | Kim et al. |

FOREIGN PATENT DOCUMENTS

| | | | | |
|---|---|---|---|---|
| CN | 1465117 | A | | 12/2003 |
| CN | 1753233 | A | | 3/2006 |
| CN | 103000942 | A | * | 3/2013 |
| CN | 109065832 | A | | 12/2018 |
| CN | 110707360 | A | | 1/2020 |
| CN | 111244546 | A | | 6/2020 |
| CN | 111900477 | A | | 11/2020 |
| CN | 112956063 | A | | 6/2021 |
| CN | 113381071 | A | | 9/2021 |
| EP | 3944392 | A1 | | 1/2022 |
| JP | 2962782 | B2 | | 10/1999 |
| JP | 4820535 | B2 | | 11/2011 |
| JP | 2019160615 | A | | 9/2019 |
| JP | 6948227 | B2 | | 10/2021 |
| KR | 20170096423 | A | | 8/2017 |
| KR | 20190027190 | A | | 3/2019 |
| WO | 2021034141 | A1 | | 2/2021 |

OTHER PUBLICATIONS

International Search Report for PCT/KR2022/014922 mailed Dec. 27, 2022. 3 pages.

Extended European Search Report including Written Opinion for Application No. 22878858.4, dated Mar. 26, 2025. 10 pages.

* cited by examiner

*Primary Examiner* — Carlos Barcena

(74) *Attorney, Agent, or Firm* — Lerner David LLP

(57) ABSTRACT

The present disclosure relates to a lithium secondary battery in which an abnormal voltage drop phenomenon is improved. The lithium secondary battery comprises a negative electrode comprising a negative electrode active material, a positive electrode comprising a positive electrode active material represented by Formula 1, a separator disposed between the positive electrode and the negative electrode, and a non-aqueous electrolyte solution, wherein the non-aqueous electrolyte solution comprises a lithium salt, a non-aqueous organic solvent, a compound represented by Formula 2 as a first additive, and lithium difluorophosphate as a second additive:

$Li_aNi_xCO_yM^1_zM^2_wO_2$ [Formula 1]

[Formula 2]

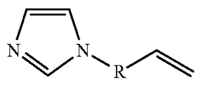

wherein all the variables are described herein.

13 Claims, No Drawings

LITHIUM SECONDARY BATTERY

CROSS-REFERENCE TO RELATED APPLICATIONS

This application is a national phase entry under 35 U.S.C. § 371 of International Application No. PCT/KR2022/014922 filed on Oct. 4, 2022, which claims priority from Korean Patent Applications No. 10-2021-0133482 filed on Oct. 7, 2021, and No. 10-2022-0125821 filed on Sep. 30, 2022, all the disclosures of which are incorporated by reference herein.

TECHNICAL FIELD

The present disclosure relates to a lithium secondary battery with improved battery durability.

BACKGROUND ART

As dependence on electric energy increases in modern society, there has been emerging research on renewable energy capable of increasing the production of electric energy without causing environmental problems.

As renewable energy exhibits intermittent power generation characteristics, a large-capacity power storage device is essential in order to stably supply power. Among such power storage devices, lithium-ion batteries have been commercialized as a device having a high energy density and thus are in the spotlight.

Lithium-ion batteries generally include a positive electrode comprising a positive electrode active material comprised of a transition metal oxide containing lithium, a negative electrode comprising a negative electrode active material capable of storing lithium ions, an electrolyte solution which is a medium for transferring lithium ions, and a separator.

The positive electrode stores energy through a redox reaction of transition metal, and leads to the fact that transition metal must be included in positive electrode materials.

The electrolyte solution for a lithium ion battery is composed of a lithium salt, an organic solvent dissolving the lithium salt, and a functional additive, wherein proper selection of these components is important to improve electrochemical properties of the battery.

Since the lithium salt contained in the non-aqueous electrolyte solution, typically $LiPF_6$, etc. is vulnerable to heat or moisture, it reacts with moisture present in the cell or is thermally decomposed to generate Lewis acids such as HF or $PF_5$. Such Lewis acid erodes and degrades a passivation film made at an electrode-electrolyte interface, thereby inducing the elution of transition metal ions from the positive electrode due to side reactions between the exposed positive electrode surface and the electrolyte solution.

In particular, when a High-Ni positive electrode active material having a Ni content greater than 0.5 is used, the elution of transition metals from the positive electrode and collapse of the positive electrode structure are easier due to deformation and collapse of a crystal structure of the positive electrode during repetitive charging and discharging processes or upon exposure to high temperatures. While the eluted transition metal is electrodeposited on the surface of the negative electrode after it moves to the negative electrode through the electrolyte solution to cause the destruction and regeneration reactions of a Solid Electrolyte Interphase (SEI) film and consumption of additional lithium ions, this causes an increase in resistance, capacity degradation, and an abnormal voltage drop phenomenon of the battery, and further accelerates the decomposition of an electrolyte solvent to accelerate gas generation. Thus, there is a problem of deteriorating stability and high-temperature durability of the secondary battery.

Therefore, in order to improve this problem, there have been ongoing studies to develop lithium secondary batteries using a non-aqueous electrolyte solution of a specific constituent capable of removing by-products (HF, $PF_5$, etc.) generated by the thermal decomposition of lithium salts and forming a stable film on the surface of an electrode, together with a positive electrode comprising a positive electrode active material of a specific constituent.

Technical Problem

An aspect of the present invention provides a lithium secondary battery with improved high-temperature stability, high-temperature cycle characteristics and abnormal voltage drop by using a positive electrode comprising a positive electrode active material of a specific constituent together with a non-aqueous electrolyte solution containing two additives capable of forming a stable ion conductive film on the electrode surface.

Technical Solution

According to an embodiment, the present disclosure provides a lithium secondary battery including a negative electrode comprising a negative electrode active material, a positive electrode comprising a positive electrode active material represented by the following Formula 1, a separator disposed between the negative electrode and the positive electrode, and a non-aqueous electrolyte solution, wherein the non-aqueous electrolyte solution comprises a lithium salt; a non-aqueous organic solvent; a compound represented by the following Formula 2 as a first additive; and lithium difluorophosphate as a second additive:

$$Li_aNi_xCo_yM^1_zM^2_wO_2 \quad \text{[Formula 1]}$$

In Formula 1, $M^1$ is Mn, Al, or a combination thereof, $M^2$ is at least one selected from a group consisting of Al, Zr, W, Ti, M, Ca and Sr, wherein $0.8 \le a \le 1.2$, $0.7 \le x < 1$, $0 < y < 0.3$, $0 < z < 0.3$, $0.01 < w \le 0.2$.

[Formula 2]

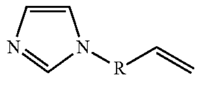

In Formula 2,

R is an alkylene group having 1 to 5 carbon atoms.

The weight ratio of the compound represented by Formula 2 and lithium difluorophosphate may be 1:2 to 1:15.

Advantageous Effects

The lithium secondary battery of the present disclosure uses a positive electrode comprising a positive electrode active material of a specific constituent and a non-aqueous electrolyte solution including specific additive such as an imidazole-based compound in which a vinyl group is substituted in the structure and a lithium difluorophosphate to form a electrochemically stable ion conductive film on the surface of the positive electrode while effectively scavenging Lewis acids ($PF_5$) generated as an electrolyte decomposition product so that it may achieve a lithium secondary battery in which high-temperature stability, high-temperature cycle characteristics, and an abnormal voltage drop phenomenon are improved.

DETAILED DESCRIPTION

Hereinafter, the present disclosure will be described in more detail.

It will be understood that words or terms used in the specification and claims of the present disclosure shall not be interpreted as the meaning defined in commonly used dictionaries, and it will be further understood that the words or terms should be interpreted as having a meaning that is consistent with their meaning in the context of the relevant art and the technical idea of the invention, based on the principle that an inventor may properly define the meaning of the words or terms to best explain the invention.

Meanwhile, the terms used herein are used only to describe exemplary embodiments, and are not intended to limit the present disclosure. Singular forms are intended to include plural forms as well, unless the context clearly indicates otherwise. It should be appreciated that the terms such as "including", "comprising", or "having" as used herein are intended to embody specific features, numbers, steps, elements, and/or combinations thereof, and does not exclude existence or addition of other specific features, numbers, steps, elements, and/or combinations thereof.

Before describing the present disclosure, the expressions "a" and "b" in the description of "a to b carbon atoms" in the specification each denote the number of carbon atoms included in a specific functional group. That is, the functional group may include "a" to "b" carbon atoms. For example, "an alkyl group having 1 to 5 carbon atoms" denotes an alkyl group containing 1 to 5 carbon atoms, i.e., $—CH_3$, $—CH_2CH_3$, $—CH_2CH_2CH_3$, $—CH_2(CH_3)CH_3$, $—CH(CH_3)CH_3$ and $—CH(CH_3)CH_2CH_3$ and the like.

Also, unless otherwise defined in the specification, the expression "substitution" denotes that at least one hydrogen bonded to carbon is substituted with an element other than hydrogen, for example, an alkyl group having 1 to 5 carbon atoms or a fluorine element.

In the present specification, the expression "%" denotes wt % unless explicitly stated otherwise.

In general, since an amount of available lithium ions in a battery is reduced while transition metals are easily eluted from an electrolyte solution due to hydrogen fluoride (HF) generated from the electrolyte solution during battery operation or structural variation of the positive electrode according to repeated charge and discharge, the capacity of the battery may be degraded. In addition, the eluted transition metal ions are re-deposited on the positive electrode to increase the resistance of the positive electrode. Also, the transition metals move to a negative electrode through the electrolyte solution to destruct a solid electrolyte interphase (SEI) or are electrodeposited on a surface of the negative electrode to cause an internal short circuit of the battery while growing into dendrites. This series of reactions promotes an electrolyte solution decomposition reaction to increase interfacial resistance of the negative electrode and brings out an additional low voltage failure as self-discharge of the negative electrode is caused.

The present disclosure provides a lithium secondary battery including a non-aqueous electrolyte solution for a lithium secondary battery comprising two additives capable of suppressing the additional elution of the transition metal by forming a robust film on a surface of the positive electrode and negative electrode as well as preventing the electrodeposition on the negative electrode by scavenging the transition metal ions, which is a cause of such degradation and failure operation.

Lithium Secondary Battery

According to an embodiment, the present disclosure provides a lithium secondary battery including a negative electrode comprising a negative electrode active material, a positive electrode comprising a positive electrode active material represented by the following Formula 1, a separator disposed between the negative electrode and the positive electrode, and a non-aqueous electrolyte solution, wherein a non-aqueous electrolyte solution includes a lithium salt, a non-aqueous organic solvent, a compound represented by the following Formula 2 as a first additive, and lithium difluorophosphate as a second additive:

$$Li_aNi_xCo_yM^1_zM^2_wO_2 \qquad \text{[Formula 1]}$$

In Formula 1, $M^1$ is Mn, Al, or a combination thereof, $M^2$ is at least one selected from a group consisting of Al, Zr, W, Ti, M, Ca and Sr, wherein $0.8 \leq a \leq 1.2$, $0.7 \leq x < 1$, $0 < y < 0.3$, $0 < z < 0.3$, $0.01 < w \leq 0.2$.

[Formula 2]

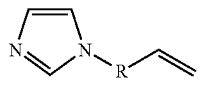

In Formula 2,

R is an alkylene group having 1 to 5 carbon atoms.

The lithium secondary battery of the present disclosure may be prepared by forming an electrode assembly, in which a positive electrode, a negative electrode, and a separator disposed between the positive electrode and the negative electrode are sequentially stacked, accommodating the electrode assembly in a battery case, and then injecting the non-aqueous electrolyte solution of the present disclosure. The lithium secondary battery of the present disclosure may be prepared according to a conventional method known in the art and used, and a method of preparing the lithium secondary battery of the present disclosure is specifically as described below.

Hereinafter, each component constituting the lithium secondary battery of the present disclosure will be described in more detail.

(1) Negative Electrode

Next, the negative electrode of the present disclosure will be described.

The negative electrode according to the present disclosure may include a negative electrode active material layer comprising a negative electrode active material, and if necessary, the negative electrode active material layer may further include a conductive agent and/or a binder.

As the negative electrode active material, various negative electrode active materials used in the art, for example, a carbon-based negative electrode active material, a silicon-based negative electrode active material, or a mixture thereof may be used.

According to an embodiment, the negative electrode active material may include a carbon-based negative electrode active material, and, as the carbon-based negative electrode active material, various carbon-based negative electrode active materials used in the art, for example, a graphite-based materials such as natural graphite, artificial graphite, or Kish graphite; high-temperature sintered carbon such as pyrolytic carbon, mesophase pitch based carbon fiber, meso-carbon microbeads, mesophase pitches, petroleum or coal tar pitch derived cokes; soft carbon; or hard carbon may be used. A shape of the carbon-based negative electrode active material is not particularly limited, and materials of various shapes, such as an irregular shape, planar shape, flaky shape, spherical shape, or fibrous shape, may be used.

Preferably, the negative electrode active material may include at least one of the carbon-based negative electrode active materials from natural graphite or artificial graphite, and the natural graphite and the artificial graphite may be used together to increase adhesion with the current collector and suppress exfoliation of the active material.

According to another embodiment, the negative electrode active material may include a silicon-based negative electrode active material together with the carbon-based negative electrode active material.

The silicon-based negative electrode active material may include at least one of, for example, Si, $SiO_x$ (where $0<x<2$), SiC or a Si—Y alloy (where the Y is an element selected from the group consisting of alkali metal, alkaline earth metal, a Group 13 element, a Group 14 element, transition metal, a rare earth element, and a combination thereof, and is not Si). The element Y may be selected from the group consisting of M, Ca, Sr, Ba, Ra, Sc, Y, Ti, Zr, Hf, Rf, V, Nb, Ta, db (dubnium), Cr, Mo, W, Tc, Re, Bh, Fe, Pb, Ru, Os, Hs, Rh, Ir, Pd, Pt, Cu, Au, Zn, Cd, B, Al, Ga, Sn, In, Ti, Ge, P, As, Sb, Bi, S, Se, Te, Po, and a combination thereof.

Since the silicon-based negative electrode active material has higher capacity characteristics compared to the carbon-based negative electrode active material, better capacity characteristics may be obtained when the silicon-based negative electrode active material is further included. However, a silicon-containing negative electrode contains more O-rich components in the SEI film compared to a graphite negative electrode, and the SEI film containing the O-rich components tends to be more easily decomposed when a Lewis acid, such as HF or $PF_5$, is present in the electrolyte solution. Thus, with respect to the negative electrode containing the silicon-based negative electrode active material, there is a need to suppress the formation of the Lewis acid, such as HF or $PF_5$, in the electrolyte solution or remove (or scavenge) the formed Lewis acid in order to maintain the stable SEI film. Since the non-aqueous electrolyte according to the present disclosure forms a stable film on the positive and negative electrodes as well as contains an electrolyte additive having the excellent effect of removing Lewis acids, it may effectively suppress the decomposition of the SEI film when the negative electrode containing the silicon-based negative electrode active material is used.

The mixing ratio of the silicon-based negative electrode active material and the carbon-based negative electrode active material may be 3:97 to 99:1, preferably 5:95 to 15:85 as a weight ratio. In a case in which the mixing ratio of the silicon-based negative electrode active material and the carbon-based negative electrode active material satisfies the above range, since a volume expansion of the silicon-based negative electrode active material is suppressed while capacity characteristics are improved, excellent cycle performance may be secured. The negative electrode active material may be included in an amount of 80 wt % to 99 wt % based on a total weight of the negative electrode active material layer. In a case in which the amount of the negative electrode active material satisfies the above range, excellent capacity characteristics and electrochemical characteristics may be obtained.

Also, the conductive agent is a component for further improving conductivity of the negative electrode active material, wherein the conductive agent may be added in an amount of 1 to 20 wt % based on the total weight of the negative electrode active material layer. Any conductive agent may be used without particular limitation as long as it has conductivity without causing adverse chemical changes in the battery, and, for example, a conductive material, such as: graphite such as natural graphite or artificial graphite; carbon black such as acetylene black, Ketjen black, channel black, furnace black, lamp black, or thermal black; conductive fibers such as carbon fibers or metal fibers; conductive powder such as fluorocarbon powder, aluminum powder, or nickel powder; conductive whiskers such as zinc oxide or potassium titanate; conductive metal oxide such as titanium oxide; or polyphenylene derivatives, may be used.

The binder is a component that assists in the binding between the conductive agent, the active material, and the current collector, wherein the binder is commonly added in an amount of 1 wt % to 30 wt % based on the total weight of the negative electrode active material layer. Examples of the binder may be a fluororesin-based binder including polyvinylidene fluoride (PVDF) or polytetrafluoroethylene (PTFE); a rubber-based binder including a styrene-butadiene rubber (SBR), an acrylonitrile-butadiene rubber, or a styrene-isoprene rubber; a cellulose-based binder including carboxymethyl cellulose (CMC), starch, hydroxypropyl cellulose, or regenerated cellulose; a poly alcohol-based binder including polyvinyl alcohol; a polyolefin-based binder including polyethylene or polypropylene; a polyimide-based binder; a polyester-based binder; and a silane-based binder.

The negative electrode may be prepared by a method of preparing a negative electrode which is known in the art. For example, the negative electrode may be prepared by a method in which a negative electrode collector is coated with a negative electrode active material slurry, which is prepared by dissolving or dispersing the negative electrode active material on the negative electrode current collector as well as selectively the binder and the conductive agent in a solvent, rolled and dried, or may be prepared by casting the negative electrode active material slurry on a separate support and then laminating a film separated from the support on the negative electrode collector.

The negative electrode collector may typically have a thickness of 3 μm to 500 μm. The negative electrode collector is not particularly limited as long as it has high conductivity without causing adverse chemical changes in the battery, and for example, copper, stainless steel, aluminum, nickel, titanium, fired carbon, copper or stainless steel that is surface-treated with one of carbon, nickel, titanium, silver, or the like, and an aluminum-cadmium alloy may be used. Similar to the positive electrode collector, microscopic irregularities may be formed on the surface of the collector to improve the adhesion of the negative electrode active material. The negative electrode collector, for example, may be used in various shapes such as that of a film, a sheet, a foil, a net, a porous body, a foam body, a non-woven fabric body, and the like.

The solvent may include water or an organic solvent, such as NMP and alcohol, and may be used in an amount such that desirable viscosity is obtained when the negative electrode active material as well as selectively the binder and the conductive agent are included. For example, the solvent may be included in an amount such that a concentration of the solid content in the active material slurry including the negative electrode active material as well as selectively the binder and the conductive agent is in a range of 50 wt % to 75 wt %, preferably, 40 wt % to 70 wt %

(2) Positive Electrode

Next, a positive electrode will be described.

The positive electrode according to the present disclosure may include a positive electrode active material layer comprising a positive electrode active material, and, if necessary, the positive electrode active material layer may further include a conductive agent and/or a binder.

The positive electrode active material may include a lithium-nickel-cobalt-manganese-transition metal (M) oxide represented by the following Formula 1.

$$Li_aNi_xCo_yM^1_zM^2_wO_2 \quad \text{[Formula 1]}$$

In Formula 1, $M^1$ is Mn, Al, or a combination thereof, and preferably may be Mn or Mn and Al.

$M^2$ is one or more selected from a group consisting of Al, Zr, W, Ti, M, Ca and Sr, and may be preferably at least one selected from the group consisting of Al, Zr, Y, M, and Ti, more preferably, may be Al.

The a represents the molar ratio of lithium in a lithium nickel-based oxide, and may be $0.8 \le a \le 1.2$, specifically $0.85 \le a \le 1.15$, or more specifically, $0.9 \le a \le 1.05$. When the molar ratio of lithium satisfies the above range, the crystal structure of the lithium nickel-based oxide may be stably formed.

The x represents the molar ratio of nickel among all metals except lithium in the lithium nickel-based oxide, and may be $0.7 \le x < 1$, specifically $0.75 \le x \le 0.99$, more specifically $0.8 \le x \le 0.95$, and more specifically $0.85 \le x \le 0.95$. When the molar ratio of nickel satisfies the above range, high energy density is exhibited and high capacity may be achieved.

The y represents the molar ratio of cobalt among all metals except lithium in the lithium nickel-based oxide, and may be $0 < y < 0.3$, preferably $0.001 < y < 0.3$, specifically $0.01 < y < 0.25$, more specifically $0.01 \le y < 0.20$, and more specifically $0.01 \le y < 0.15$. When the molar ratio of cobalt satisfies the above range, good resistance characteristics and output characteristics may be achieved.

The z represents the molar ratio of a $M^1$ element among all metals except lithium in the lithium nickel-based oxide, and may be $0.001 < z < 0.25$, preferably $0.01 \le z < 0.20$, more preferably $0.01 \le z < 0.20$, and more specifically $0.01 \le z < 0.15$. When the molar ratio of the $M^1$ element satisfies the above range, the structural stability of the positive electrode active material is exhibited to be excellent.

The w represents the molar ratio of a $M^2$ element among all metals except lithium in the lithium nickel-based oxide, and may be $0.01 < w \le 0.2$, specifically $0.01 < w \le 0.1$, and preferably $0.01 < w \le 0.05$.

Specifically, the single-particle-based positive electrode active material may include $Li(Ni_{0.8}Co_{0.15}Al_{0.05})O_2$, $Li(Ni_{0.85}Mn_{0.08}Co_{0.05}Al_{0.02})O_2$, $Li(Ni_{0.86}Mn_{0.07}Co_{0.05}Al_{0.02})O_2$, $Li(Ni_{0.87}Mn_{0.07}Co_{0.04}Al_{0.02})O_2$, or $Li(Ni_{0.90}Mn_{0.03}Co_{0.05}Al_{0.02})O_2$ having a Ni content greater than 80 mole % based on a total mole number of the transition metal in order to achieve a high-capacity battery.

In a case in which a high-Ni lithium transition metal oxide having a Ni content greater than 0.7 is used as the positive electrode active material, since sizes of $Li^+$ ion and $Ni^{2+}$ ion are similar to each other, a cation mixing phenomenon occurs in which positions of the $Li^+$ ion and the $Ni^{2+}$ ion are changed each other in a layered structure of the positive electrode active material during charge and discharge process. That is, a nickel transition metal having a d orbital must have an octahedron structure during coordinate bonding in an environment, such as a high temperature, according to a change in oxidation number of Ni contained in the positive electrode active material, but a crystal structure of the positive electrode active material may be deformed and collapsed while a twisted octahedron is formed by a non-uniform reaction in which the order of the energy level is reversed or the oxidation number is changed by external energy supply. Furthermore, since another side reaction, in which a transition metal, particularly, a nickel metal is eluted from the positive electrode active material, occurs due to a side reaction between the positive electrode active material and the electrolyte solution during high-temperature storage, overall performance of the secondary battery is degraded due to the structural collapse of the positive electrode active material along with the depletion of the electrolyte solution.

The present disclosure may solve this problem by using a positive electrode containing a high content of nickel transition metal oxide together with a non-aqueous electrolyte solution containing a specific additive. That is, the non-aqueous electrolyte solution including an additive with a specific configuration is used, a robust ion conductive film is formed on a surface of the positive electrode to suppress the cation mixing phenomenon of the $Li^+$ ion and the $Ni^{2+}$ ion and to effectively suppress the side reaction between the positive electrode and the electrolyte solution and the metal elution phenomenon, and thus, the structural instability of the high-capacity electrode may be alleviated. Therefore, since the sufficient amount of the nickel transition metal for ensuring the capacity of the lithium secondary battery may be secured, the energy density may be increased to prevent a decrease in output characteristics.

The positive electrode active material may be present in an amount of 80 wt % to 99 wt %, specifically, 90 wt % to 99 wt % based on the total weight of the positive electrode active material layer. Here, when the amount of the positive electrode active material is 80 wt % or less, energy density is reduced, and thus capacity may be reduced.

The conductive agent is not particularly limited as long as it has conductivity without causing adverse chemical changes in the battery, and, for example, carbon powder, such as carbon black, acetylene black, Ketjen black, channel black, furnace black, lamp black or thermal black; graphite powder such as natural graphite, artificial graphite, or graphite with a highly developed crystal structure; conductive fibers such as carbon fibers or metal fibers; conductive powder such as fluorocarbon powder, aluminum powder, or nickel powder; conductive whiskers such as zinc oxide or potassium titanate; conductive metal oxide such as titanium oxide; or polyphenylene derivatives, may be used. The conductive agent is added in an amount of 1 wt % to 30 wt % based on the total weight of the positive electrode active material layer.

The binder is a component that assists in the binding between the positive electrode active material particles and the binding between the positive electrode active material and the current collector, wherein the binder is commonly added in an amount of 1 wt % to 30 wt % based on the total weight of the positive electrode active material layer. Examples of the binder may be a fluororesin-based binder including polyvinylidene fluoride (PVDF) or polytetrafluoroethylene (PTFE); a rubber-based binder including a styrene-butadiene rubber (SBR), an acrylonitrile-butadiene rubber, or a styrene-isoprene rubber; a cellulose-based binder including carboxymethyl cellulose (CMC), starch, hydroxypropyl cellulose, or regenerated cellulose; a poly alcohol-based binder including polyvinyl alcohol; a polyolefin-based binder including polyethylene or polypropylene; a polyimide-based binder; a polyester-based binder; and a silane-based binder.

The positive electrode may be prepared by a method of preparing a positive electrode which is known in the art. For example, the positive electrode may be prepared by a method in which a positive electrode current collector is coated with a positive electrode slurry, which is prepared by dissolving or dispersing the positive electrode active material, the binder and/or the conductive agent in a solvent, and then rolled and dried, or may be prepared by casting the positive electrode active material layer on a separate support and then laminating a film separated from the support on the positive electrode collector.

The positive electrode collector is not particularly limited as long as it has conductivity without causing adverse chemical changes in the battery, and, for example, stainless steel, aluminum, nickel, titanium, fired carbon, or aluminum or stainless steel that is surface-treated with carbon, nickel, titanium, silver, or the like may be used. The solvent may include an organic solvent such as NMP (N-methyl-2-pyrrolidone), and may be used in an amount such that desirable viscosity is obtained when the positive electrode active material as well as selectively the binder and the conductive agent are included. For example, the solvent may be included in an amount such that a concentration of the solid content in the active material slurry including the positive electrode active material as well as selectively the binder and the conductive agent is in a range of 10 wt % to 90 wt %, preferably, 30 wt % to 80 wt %

(3) Separator

A typically used porous polymer film, for example, a porous polymer film prepared from a polyolefin-based polymer, such as an ethylene homopolymer, a propylene homopolymer, an ethylene/butene copolymer, an ethylene/hexene copolymer, or an ethylene/methacrylate copolymer, may be used alone or in a lamination therewith as the separator included in the lithium secondary battery of the present disclosure, or a typical porous nonwoven fabric, for example, a nonwoven fabric formed of high melting point glass fibers or polyethylene terephthalate fibers may be used, but the present disclosure is not limited thereto.

(4) Non-Aqueous Electrolyte Solution

Next, the non-aqueous electrolyte solution of the present disclosure will be described.

The non-aqueous electrolyte solution of the present disclosure may include a lithium salt; a non-aqueous organic solvent; a compound represented by Formula 2 as a first additive; and lithium difluorophosphate as a second additive, and selectively may further include a third additive.

(4-1) Lithium Salt

First, a lithium salt will be described.

Any lithium salt typically used in a non-aqueous electrolyte solution for a lithium secondary battery may be used as the lithium salt without limitation, and for example, the lithium salt may include $Li^+$ as a cation, and may include at least one of $F^-$, $Cl^-$, $Br^-$, $I^-$, $NO_3^-$, $N(CN)_2^-$, $BF_4^-$, $ClO_4^-$, $B_{10}Cl_{10}^-$, $AlCl_4^-$, $AlO_4^-$, $PF_6^-$, $SO_3F^-$, $CF_3SO_3^-$, $CH_3CO_2^-$, $CF_3CO_2^-$, $AsF_6^-$, $SbF_6^-$, $CH_3SO_3^-$, $(CF_3CF_2SO_2)_2N^-$, $(CP_3SO_2)_2N^-$, $(FSO_2)_2N^-$, $(PO_2F_2)^-$, $(FSO_2)(POF_2)N^-$, $BF_2C_2O_4^-$, $BC_4O_8^-$, $PF_4C_2O_4^-$, $PF_2C_4O_8^-$, $(CF_3)_2PF_4^-$, $(OF_3)_3PF_3^-$, $(OF_3)_4PF_2^-$, $(CF_3)_5PF^-$, $(CF_3)_6P^-$, $C_4F_9SO_3^-$, $CF_3CF_2SO_3^-$, $CF_3CF_2(OF_3)_2CO^-$, $(CF_3SO_2)_2CH^-$, $CF_3(CF_2)_7SO_3^-$ or $SCN^-$ as an anion.

Specifically, the lithium salt may include a single material of LiCl, LiBr, LiI, $LiBF_4$, $LiClO_4$, $LiB_{10}Cl_{10}$, $LiAlCl_4$, $LiAlO_4$, $LiPF_6$, $LiSO_3F$, $LiCF_3SO_3$, $LiCH_3CO_2$, $LiCF_3CO_2$, $LiAsF_6$, $LiSbF_6$, $LiCH_3SO_3$, $LiN(SO_2F)_2$ (Lithium bis(fluorosulfonyl)imide, LiFSI), $LiN(SO_2CF_2CF_3)_2$ (lithium bis (pentafluoroethanesulfonyl) imide, LiBETI) or $LiN(SO_2CF_3)_2$ (lithium bis(trifluoromethanesulfonyl) imide, LiTFSI), or a mixture of two or more thereof. In addition to these materials, lithium salts commonly used in electrolyte solutions of lithium secondary batteries may be used without limitation. Specifically, the lithium salt may include $LiPF_6$.

The lithium salt may be appropriately changed within a generally usable range, but may be included in a concentration of 0.8 M to 3.0 M, specifically, 1.0M to 3.0M in the electrolyte solution to obtain the optimal effect of forming an anti-corrosive film on a surface of an electrode. In a case in which the concentration of the lithium salt is in the above concentration range, viscosity of the non-aqueous electrolyte solution may be controlled to achieve the optimal impregnability, and the effects of improving the capacity and cycle characteristics of a lithium secondary battery may be obtained by improving the mobility of lithium ions.

(4-2) Non-Aqueous Organic Solvent

Further, the non-aqueous organic solvent will be described.

Various non-aqueous organic solvents typically used in a non-aqueous electrolyte solution may be used as the non-aqueous organic solvent without limitation. The non-aqueous organic solvent is not limited as long as it may minimize decomposition due to an oxidation reaction during charge and discharge of the secondary battery and may exhibit desired characteristics with the additive.

Specifically, the non-aqueous organic solvent having higher ion conductivity may include at least one of a highly viscous cyclic carbonate-based compound, which well dissociates lithium salts due to high permittivity or a linear carbonate-based compound having low viscosity and low permittivity.

The cyclic carbonate-based compound may include at least one of ethylene carbonate (EC), propylene carbonate (PC), 1,2-butylene carbonate, 2,3-butylene carbonate, 1,2-pentylene carbonate, 2,3-pentylene carbonate, or vinylene carbonate, and among them, may include ethylene carbonate.

The linear carbonate-based compound may include at least one of dimethyl carbonate (DMC), diethyl carbonate (DEC), dipropyl carbonate, ethylmethyl carbonate (EMC), methylpropyl carbonate, or ethylpropyl carbonate, and specifically may include ethylmethyl carbonate (EMC).

In the present disclosure, a mixture of the cyclic carbonate-based compound and the linear carbonate-based compound may be used wherein a mixing ratio of the cyclic carbonate-based compound to the linear carbonate-based compound may be in a range of 10:90 to 80:20 by volume, and specifically may be 30:70 to 50:50 by volume. In a case where the mixing ratio of the cyclic carbonate-based compound and the linear carbonate-based compound satisfies the above range, a non-aqueous electrolyte solution having a higher electrical conductivity may be prepared.

Also, a propionate compound may be further mixed as the non-aqueous organic solvent in order to improve the disadvantages of the carbonate-based compound and increase stability during high-temperature and high-voltage driving.

The propionate compound may include at least one of methyl propionate, ethyl propionate (EP), propyl propionate or butyl propionate. Specifically, it may include at least one of ethyl propionate or propyl propionate.

In the non-aqueous electrolyte solution, other components except for the non-aqueous organic solvent, for example, a remainder except for lithium salts, oligomers, and selectively included additives, may be non-aqueous organic solvents unless otherwise stated.

(4-3) First Additive

The non-aqueous electrolyte solution for a lithium secondary battery of the present disclosure may include a compound represented by the following Formula 2 as a first additive.

(Formula 2)

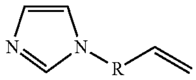

In Formula 2,

R is an alkylene group having 1 to 5 carbon atoms.

The R may further comprise at least one unsaturated bond.

The compound represented by Formula 2 includes an imidazole structure capable of acting as a Lewis base. Thus, the nitrogen atom of the imidazole group may effectively scavenge a Lewis acid generated as a decomposition product of a lithium salt. When the battery reaches a predetermined voltage during charging and discharging processes, the vinyl group included in the structure of the compound represented by Chemical Formula 2 is reduced on the surface of the negative electrode to form an ion conductive film on the surface of the negative electrode. This ion conductive film may suppress additional decomposition reactions of the electrolyte solution. This can also improve cycle life characteristics and high-temperature storage performance by facilitating the insertion and extraction of lithium ions from the negative electrode during repetitive charging and discharging processes or high-temperature storage, and may improve an increase in the resistance rate by effectively preventing electrodeposition of lithium ions caused by eluted transition metals or overvoltage.

Specifically, in Formula 2, R may be an alkylene group having 1 to 3 carbon atoms. More specifically, the compound represented by Formula 2 may be a compound represented by the following Formula 2a.

[Formula 2a]

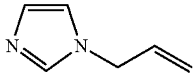

The compound represented by Formula 2 may be included in an amount of 0.1 wt % to 5.0 wt % based on the total weight of the non-aqueous electrolyte solution.

In a case in which the compound represented by Formula 2 is included in the above range, secondary batteries with further improved overall performance may be manufactured. For example, when the amount of the first additive is 0.1 wt % or more, a stabilizing effect or elution suppressing effect may be obtained during the formation of a SEI film while suppressing an increase in resistance so that an effect of improving an abnormal voltage drop may be obtained. Also, when the amount of the additive is 5 wt % or less, an increase in viscosity of the electrolyte solution caused by the surplus compound may be prevented and an increase in battery resistance may be effectively prevented by suppressing excessive film formation. As a result, the maximum elution suppressing effect may be obtained within the increase in resistance which may be accommodated.

Specifically, when the compound represented by Formula 2 is included in an amount of 0.3 wt % to 3.0 wt %, specifically 0.3 wt % to 2.5 wt %, based on the total weight of the non-aqueous electrolyte solution, secondary batteries with further improved overall performance may be manufactured.

(4-4) Second Additive

In addition, the non-aqueous electrolyte solution of the present disclosure may form a film containing an inorganic component on the surface of the positive electrode and having improved thermal stability by mixing a lithium salt-type additive such as lithium difluorophosphate (LiDFP) as a second additive.

The lithium difluorophosphate is a component for achieving an effect of improving long-term life characteristics of the secondary battery, wherein, since it is electrochemically decomposed on the surfaces of the positive electrode and the negative electrode to help the formation of the ion conductive film, it may suppress metal elution from the positive electrode and may prevent side reactions between the electrode and the electrolyte solution to achieve an effect of improving high-temperature storage characteristics and cycle life characteristics of the secondary battery.

In the non-aqueous electrolyte solution of the present disclosure, the weight ratio of the compound represented by Formula 2, which is a first additive, and lithium difluorophosphate, which is a second additive, may be 1:2 to 1:15. In a case in which the compound represented by Formula 2 and lithium difluorophosphate are included within the above range, and the effect of removing decomposition products generated from lithium salts is further improved while a film having excellent thermal stability is formed on the surface of the electrode so that the output of the secondary battery may be improved.

Specifically, the compound represented by Formula 2 and lithium difluorophosphate may be included in a weight ratio of 1:2 to 1:10, more specifically, 1:2 to 1:7.

In a case in which the compound represented by Formula 2 and lithium difluorophosphate are included in an equivalent amount, for example, 1:1, components having high ion conductivity generated from decomposition of lithium difluorophosphate are relatively reduced and the organic film derived from the compound represented by Formula 2 is formed relatively thickly, the initial film resistance may increase and the overpotential may intensify. As a result, when used with a positive electrode active material using a lithium transition metal oxide with high nickel (Ni) content, in which the Ni content is greater than 0.7, it may accelerate the decomposition of the electrolyte solution and the aging speed of the active material, and thus long-term durability (cycle characteristics, etc.) may be relatively degraded.

(4-5) Third Additive

Also, in order to prevent the non-aqueous electrolyte solution from being decomposed to cause collapse of the negative electrode in a high output environment, or further improve low-temperature high-rate discharge characteristics, high-temperature stability, overcharge protection, and a battery swelling suppression effect at high temperatures, the non-aqueous electrolyte solution for a lithium secondary battery of the present disclosure may further include another additional third additive in addition to the above two additives, if necessary.

Examples of the third additive may be at least one selected from the group consisting of a cyclic carbonate-based compound, a halogen-substituted carbonate-based compound, a sultone-based compound, a sulfate-based compound, a phosphate-based or phosphite-based compound, a borate-based compound, a benzene-based compound, an amine-based compound, an imidazole-based compound, a silane-based compound, and a lithium salt-based compound.

The cyclic carbonate-based compound may include vinylene carbonate (VC) or vinyl ethylene carbonate (VEC).

The halogen-substituted carbonate-based compound may include fluoroethylene carbonate (FEC), etc.

As a specific example, the sultone-based compound may include at least one of 1,3-propane sultone (PS), 1,4-butane sultone, ethane sultone, 1,3-propene sultone (PRS), 1,4-butene sultone, or 1-methyl-1,3-propene sultone.

As a specific example, the sulfate-based compound may be ethylene sulfate (Esa), trimethylene sulfate (TMS), or methyl trimethylene sulfate (MTMS).

The phosphate-based or phosphite-based compound, for example, may be at least one selected from the group consisting of lithium difluoro(bisoxalato)phosphate, lithium tetrafluoro oxalato phosphate, tris(trimethylsilyl)phosphate, tris(trimethylsilyl)phosphite, tris(2,2,2-trifluoroethyl)phosphate, and tris(trifluoroethyl)phosphite.

The borate-based compound, for example, may include tetraphenylborate, lithium oxalyldifluoroborate (LiODFB) or lithium bis(oxalato)borate ($LiB(C_2O_4)_2$, LiBOB) capable of forming a film on the surface of the negative electrode.

The benzene-based compound may be fluorobenzene, and the amine-based compound may be triethanolamine or ethylenediamine.

The imidazole-based compound may be lithium 2-trifluoromethyl-4,5-dicyanoimidazole, 1-methyl,5-propargyl imidazole, propargyl 1H-imidazole-1-carboxylate), 11-vinyl imidazole, or allyl 1H-imidazole-1-carboxylate.

The silane-based compound may be tetravinylsilane.

The lithium salt-based compound is a compound different from the lithium salt included in the non-aqueous electrolyte solution, wherein the lithium salt-based compound may include $LiPO_2F_2$, $LiSO_3F$ or $LiBF_4$.

Among these third additives, in order to form a more robust SEI film on the surface of the negative electrode during an initial activation process, other additives having an excellent effect of forming a film on the surface of the negative electrode, specifically at least one selected from the group consisting of vinylene carbonate, 1,3-propanesultone, ethylene sulfate, fluoroethylene carbonate (FEC), and $LiBF_4$ may be included.

The third additive may be used by mixing two or more types of compounds, and may be included in an amount of 0.01 wt % to 50 wt %, particularly 0.01 wt % to 20 wt %, and preferably 0.05 wt % to 15 wt % based on the total weight of the non-aqueous electrolyte solution. If the amount of the other additive is in the above range, it is desirable because the high-temperature storage characteristics and cycle life characteristics may be improved, the side reaction caused by adding the excessive amount of the additive may be prevented, and precipitation or remaining of the unreacted material may be prevented.

A shape of the lithium secondary battery of the present disclosure is not particularly limited, but a cylindrical type using a can, a prismatic type, a pouch type, or a coin type may be used.

Hereinafter, the present disclosure will be described in more detail according to examples. However, the invention may be embodied in many different forms and should not be construed as being limited to the embodiments set forth herein. Rather, these example embodiments are provided so that this description will be thorough and complete, and will fully convey the scope of the present disclosure to those skilled in the art.

EXAMPLES

Example 1

(Preparation of Non-Aqueous Electrolyte Solution)

After dissolving $LiPF_6$ in a non-aqueous organic solvent, in which ethylene carbonate (EC) and ethylmethyl carbonate (EMC) were mixed in a volume ratio of 30:70, such that a concentration of the $LiPF_6$ was 1.0 M, a non-aqueous electrolyte solution was prepared by adding 0.1 wt % of the compound represented by Formula 2a, 1.0 wt % of lithium difluorophosphate, and as a third additive, 0.5 wt % of vinylene carbonate (VC), 0.5 wt % of 1,3-propanesultone (PS), and 1.0 wt % of ethylene sulfate (ESa) (see Table 1 below).

(Preparation of Secondary Battery)

A positive electrode active material ($Li(Ni_{0.85}Mn_{0.08}Co_{0.05}Al_{0.02})O_2$), a conductive agent (carbon black), and a binder (polyvinylidene fluoride) were added to N-methyl-2-pyrrolidone (NMP) as a solvent, at a weight ratio of 97.6:0.8:1.6 to prepare a positive electrode active material slurry (solid content 72 wt %). A 13.5 μm thick positive electrode collector (Al thin film) was coated with the positive electrode active material slurry, dried, and roll-pressed to prepare a positive electrode. A negative electrode active material (artificial graphite and natural graphite=80:20 weight ratio), a binder (SBR-CMC), and a conductive agent (carbon black) were added to NMP, as a solvent, at a weight ratio of 95.6:3.4:1.0 to prepare a negative electrode active material slurry (solid content: 50 wt %). A 6 μm thick negative electrode collector (Cu thin film) was coated with the negative electrode active material slurry, dried, and roll-pressed to prepare a negative electrode.

After an electrode assembly was prepared by sequentially stacking the positive electrode, a polyolefin-based porous separator coated with inorganic particles ($Al_2O_3$), and the negative electrode, the electrode assembly was put in a pouch-type secondary battery case, and the above-prepared non-aqueous electrolyte solution for a lithium secondary battery was injected to prepare a pouch-type lithium secondary battery having a driving voltage of 4.2V or higher.

Example 2

(Non-Aqueous Electrolyte Solution Preparation)

After dissolving $LiPF_6$ in a non-aqueous organic solvent such that a concentration of the $LiPF_6$ was 1.0 M, a non-aqueous electrolyte solution was prepared by adding 0.1 wt % of the compound represented by Formula 2a, 0.8 wt % of lithium difluorophosphate, and as a third additive, 0.5 wt % of vinylene carbonate (VC), 0.5 wt % of 1,3-propanesultone (PS), and 1.0 wt % of ethylene sulfate (ESa) (see Table 1 below).

(Preparation of Secondary Battery)

A lithium secondary battery was prepared in the same manner as in Example 1 except that the above-prepared non-aqueous electrolyte solution for a lithium secondary battery was injected instead of the non-aqueous electrolyte solution for a lithium secondary battery which was prepared in Example 1.

Example 3

(Preparation of Non-Aqueous Electrolyte Solution)

After dissolving $LiPF_6$ in a non-aqueous organic solvent such that a concentration of the $LiPF_6$ was 1.0 M, a non-aqueous electrolyte solution was prepared by adding 0.3 wt % of the compound represented by Formula 2a, 1.0 wt % of lithium difluorophosphate, and as a third additive, 0.5 wt % of vinylene carbonate (VC), 0.5 wt % of 1,3-propanesultone (PS), and 1.0 wt % of ethylene sulfate (ESa) (see Table 1 below).

(Preparation of Secondary Battery)

A lithium secondary battery was prepared in the same manner as in Example 1 except that the above-prepared non-aqueous electrolyte solution for a lithium secondary battery was injected instead of the non-aqueous electrolyte solution for a lithium secondary battery which was prepared in Example 1.

Example 4

(Preparation of Non-Aqueous Electrolyte Solution)

After dissolving $LiPF_6$ in a non-aqueous organic solvent such that a concentration of the $LiPF_6$ was 1.0 M, a non-aqueous electrolyte solution was prepared by adding 0.3 wt % of the compound represented by Formula 2a, 0.8 wt % of lithium difluorophosphate, and as a third additive, 0.5 wt % of vinylene carbonate (VC), 0.5 wt % of 1,3-propanesultone (PS), and 1.0 wt % of ethylene sulfate (ESa).

(Preparation of Secondary Battery)

A lithium secondary battery was prepared in the same manner as in Example 1 except that the above-prepared non-aqueous electrolyte solution for a lithium secondary battery was injected instead of the non-aqueous electrolyte solution for a lithium secondary battery which was prepared in Example 1.

Example 5

(Preparation of Non-Aqueous Electrolyte Solution)

After dissolving $LiPF_6$ in a non-aqueous organic solvent such that a concentration of the $LiPF_6$ was 1.0 M, a non-aqueous electrolyte solution was prepared by adding 0.5 wt % of the compound represented by Formula 2a, 1.0 wt % of lithium difluorophosphate, and as a third additive, 0.5 wt % of vinylene carbonate (VC), 0.5 wt % of 1,3-propanesultone (PS), and 1.0 wt % of ethylene sulfate (ESa).

(Preparation of Secondary Battery)

A lithium secondary battery was prepared in the same manner as in Example 1 except that the above-prepared non-aqueous electrolyte solution for a lithium secondary battery was injected instead of the non-aqueous electrolyte solution for a lithium secondary battery which was prepared in Example 1.

Example 6

(Preparation of Non-Aqueous Electrolyte Solution)

After dissolving $LiPF_6$ in a non-aqueous organic solvent such that a concentration of the $LiPF_6$ was 1.0 M, a non-aqueous electrolyte solution was prepared by adding 0.5 wt % of the compound represented by Formula 2a, 0.5 wt % of lithium difluorophosphate, and as a third additive, 0.5 wt % of vinylene carbonate (VC), 0.5 wt % of 1,3-propanesultone (PS), and 1.0 wt % of ethylene sulfate (ESa).

(Preparation of Secondary Battery)

A lithium secondary battery was prepared in the same manner as in Example 1 except that the above-prepared non-aqueous electrolyte solution for a lithium secondary battery was injected instead of the non-aqueous electrolyte solution for a lithium secondary battery which was prepared in Example 1.

Comparative Example 1

(Non-Aqueous Electrolyte Solution Preparation)

After dissolving $LiPF_6$ in a non-aqueous organic solvent such that a concentration of the $LiPF_6$ was 1.0 M, a non-aqueous electrolyte solution was prepared by adding 0.5 wt % of vinylene carbonate (VC), 0.5 wt % of 1,3-propanesultone (PS), and 1.0 wt % of ethylene sulfate (ESa).

(Preparation of Secondary Battery)

A lithium secondary battery was prepared in the same manner as in Example 1 except that the above-prepared non-aqueous electrolyte solution for a lithium secondary battery was injected instead of the non-aqueous electrolyte solution for a lithium secondary battery which was prepared in Example 1.

Comparative Example 2

(Non-Aqueous Electrolyte Solution Preparation)

After dissolving $LiPF_6$ in a non-aqueous organic solvent such that a concentration of the $LiPF_6$ was 1.0 M, a non-aqueous electrolyte solution was prepared by adding 1.0 wt % of lithium difluorophosphate, 0.5 wt % of vinylene carbonate (VC), 0.5 wt % of 1,3-propanesultone (PS), and 1.0 wt % of ethylene sulfate (ESa).

(Preparation of Secondary Battery)

A lithium secondary battery was prepared in the same manner as in Example 1 except that the above-prepared non-aqueous electrolyte solution for a lithium secondary battery was injected instead of the non-aqueous electrolyte solution for a lithium secondary battery which was prepared in Example 1.

Comparative Example 3

(Non-Aqueous Electrolyte Solution Preparation)

After dissolving $LiPF_6$ in a non-aqueous organic solvent such that a concentration of the $LiPF_6$ was 1.0 M, a non-aqueous electrolyte solution was prepared by adding 0.5 wt % of the compound represented by Formula 2a, 0.5 wt % of vinylene carbonate (VC), 0.5 wt % of 1,3-propanesultone (PS), and 1.0 wt % of ethylene sulfate (ESa).

(Preparation of Secondary Battery)

A lithium secondary battery was prepared in the same manner as in Example 1 except that the above-prepared non-aqueous electrolyte solution for a lithium secondary battery was injected instead of the non-aqueous electrolyte solution for a lithium secondary battery which was prepared in Example 1.

Comparative Example 4

(Non-Aqueous Electrolyte Solution Preparation)

After dissolving $LiPF_6$ in a non-aqueous organic solvent such that a concentration of the $LiPF_6$ was 1.0 M, a non-aqueous electrolyte solution was prepared by adding 0.5 wt % of the compound represented by the following Formula 3, 1.0 wt % of lithium difluorophosphate, 0.5 wt % of vinylene carbonate (VC) as a third additive, 0.5 wt % of 1,3-propanesultone (PS), and 1.0 wt % of ethylene sulfate (ESa).

[Formula 3]

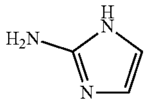

(Preparation of Secondary Battery)

A lithium secondary battery was prepared in the same manner as in Example 1 except that the above-prepared non-aqueous electrolyte solution for a lithium secondary battery was injected instead of the non-aqueous electrolyte solution for a lithium secondary battery which was prepared in Example 1.

Comparative Example 5

A lithium secondary battery was prepared in the same manner as in Example 2 except that the positive electrode was prepared by using $Li(Ni_{0.8}Mn_{0.1}Co_{0.1})O_2$ (hereinafter "NCM1") instead of $Li(Ni_{0.85}Mn_{0.08}Co_{0.05}Al_{0.02})O_2$ as a positive electrode active material.

Comparative Example 6

A lithium secondary battery was prepared in the same manner as in Example 4 except that the positive electrode was prepared by using $Li(Ni_{0.8}Mn_{0.1}Co_{0.1})O_2$ (hereinafter "NCM1") instead of $Li(Ni_{0.85}Mn_{0.08}Co_{0.05}Al_{0.02})O_2$ as a positive electrode active material.

Comparative Example 7

A lithium secondary battery was prepared in the same manner as in Example 3 except that the positive electrode was prepared by using $Li(Ni_{0.6}Mn_{0.2}Co_{0.2})O_2$ (hereinafter "NCM2") instead of $Li(Ni_{0.85}Mn_{0.08}Co_{0.05}Al_{0.02})O_2$ as a positive electrode active material.

Comparative Example 8

A lithium secondary battery was prepared in the same manner as in Example 5 except that the positive electrode was prepared by using $Li(Ni_{0.6}Mn_{0.2}Co_{0.2})O_2$ (hereinafter "NCM2") instead of $Li(Ni_{0.85}Mn_{0.08}Co_{0.05}Al_{0.02})O_2$ as a positive electrode active material.

TABLE 1

| | Non-aqueous electrolyte solution | | | | | | |
|---|---|---|---|---|---|---|---|
| | First additive | Amount (wt %) | Second additive | Amount (wt %) | Entire Amount of Third Additive (wt %) | Weight ratio of First and Second additives | Positive electrode Active material type |
| Example 1 | 2a | 0.1 | LiDFP | 1.0 | 2.0 | 1:10 | NCMA |
| Example 2 | 2a | 0.1 | LiDFP | 0.8 | 2.0 | 1:8 | |
| Example 3 | 2a | 0.3 | LiDFP | 1.0 | 2.0 | 1:3.3 | |
| Example 4 | 2a | 0.3 | LiDFP | 0.8 | 2.0 | 1:2.7 | |
| Example 5 | 2a | 0.5 | LiDFP | 1.0 | 2.0 | 1:2 | |
| Example 6 | 2a | 0.5 | LiDFP | 0.5 | 2.0 | 1:1 | |
| Comparative Example 1 | — | — | — | — | 2.0 | — | |
| Comparative Example 2 | 2a | — | LiDFP | 1.0 | 2.0 | 0:1 | |
| Comparative Example 3 | 2a | 0.5 | LiDFP | — | 2.0 | 1:0 | |
| Comparative Example 4 | 3 | 0.5 | LiDFP | 1.0 | 2.0 | 1:2 | |
| Comparative Example 5 | 2a | 0.1 | LiDFP | 0.8 | 2.0 | 1:8 | NCM1 |
| Comparative Example 6 | 2a | 0.3 | LiDFP | 0.8 | 2.0 | 1:2.7 | NCM1 |
| Comparative Example 7 | 2a | 0.3 | LiDFP | 1.0 | 2.0 | 1:3.3 | NCM2 |
| Comparative Example 8 | 2a | 0.5 | LiDFP | 1.0 | 2.0 | 1:2 | NCM2 |

In Table 1, the abbreviation of each compound has the following meaning.

NCMA: $Li(Ni_{0.85}Mn_{0.08}Co_{0.05}Al_{0.02})O_2$

NCM1: $Li(Ni_{0.8}Mn_{0.1}Co_{0.1})O_2$

NCM2: $Li(Ni_{0.6}Mn_{0.2}Co_{0.2})O_2$

EXPERIMENTAL EXAMPLE

Experimental Example 1. Evaluation of Resistance Increase Rate after High-Temperature Storage After each of the secondary batteries prepared in Examples 1 to 6 and Comparative Examples 1 to 8 was charged at a rate of 0.33 C to 4.2 V under a constant current/constant voltage condition at 25° C., each secondary battery was discharged at a rate of 0.33 C to 2.5 V under a constant current condition, which were set as one cycle. After 3 cycles of initial charging and discharging were performed, the voltage drop value confirmed when discharged at a rate of 2.5 C for 10 seconds at a SOC of 50% was measured and the initial resistance value was calculated by using the following Equation 1.

Subsequently, after each of the lithium secondary batteries prepared in Examples 1 to 6 and Comparative Examples 1 to 8 was stored at 60° C. for 3 weeks at a SOC of 100% and cooled to 25° C., the voltage drop value confirmed when discharged at a rate of 2.5 C for 10 seconds at a SOC of 50% was measured and the resistance increase rate was calculated by using the following Equation 2.

Initial discharge resistance (ohm)=(voltage before discharge−voltage after discharge) [V]/discharge current value [A] [Equation 1]

Resistance increase rate (%)={(resistance after high temperature storage−resistance before high temperature storage)/resistance before high temperature storage}×100 [Equation 2]

TABLE 2

| | Initial discharge resistance (mohm) | Resistance increase rate after high temperature storage (%) |
|---|---|---|
| Example 1 | 36.0 | 2.9 |
| Example 2 | 36.2 | 3.6 |
| Example 3 | 38.2 | −4.3 |
| Example 4 | 38.4 | 1.3 |
| Example 5 | 42.1 | −8.6 |
| Example 6 | 41.0 | 5.1 |
| Comparative Example 1 | 33.4 | 96.5 |
| Comparative Example 2 | 44.1 | 49.6 |
| Comparative Example 3 | 36.6 | 43.7 |
| Comparative Example 4 | 39.6 | 19.5 |
| Comparative Example 5 | 44.5 | 7.7 |
| Comparative Example 6 | 47.0 | 4.4 |
| Comparative Example 7 | 58.5 | 35.5 |
| Comparative Example 8 | 61.7 | 32.9 |

Referring to Table 2 above, it may be understood that the secondary batteries prepared in Examples 1 to 5 exhibited greatly reduced resistance increase rates (%) after high temperature storage compared to the lithium secondary batteries prepared in Comparative Examples 1 to 4 using a non-aqueous electrolyte solution without containing the first additive and/or second additive and in Comparative Examples 5 to 8 having positive electrodes with different positive electrode active material constituents.

It may be understood that the secondary battery prepared in Example 6 including a non-aqueous electrolyte solution containing the first additive and the second additive in the same amount exhibited a relatively increased resistance increase rate (%) after high temperature storage as the initial film resistance increased compared to those prepared in Examples 1 to 5.

Experimental Example 2. Evaluation of Initial Discharge Capacity and Discharge Capacity Retention Rate (%)

After each of the lithium secondary batteries prepared in Examples 1 to 6 and Comparative Examples 1 to 4, 7 and 8 was charged at a rate of 0.33C in a constant current-constant voltage condition at 25° C. to 4.2 V, each lithium secondary battery was discharged at a rate of 0.33 C to 2.5 V under a constant current condition, which was set as one cycle. After 3 cycles were performed, the initial discharge capacity was measured, and the results are presented in Table 3 below.

Subsequently, after storage at 60° C. for 3 weeks at a SOC of 100%, each of the lithium secondary batteries prepared in Examples 1 to 6 and Comparative Examples 1 to 4, 7 and 8 was cooled to 25° C., and the discharge capacity was then measured. The discharge capacity retention rate was calculated by using the following Equation 3, and the results thereof are presented in Table 3 below.

Discharge capacity retention rate (%)=(discharge capacity after high temperature storage at 60° C. for 3 weeks/initial discharge capacity)×100 [Equation 3]

TABLE 3

| | Initial discharge capacity (mAh) | Discharge capacity retention rate (%) after high temperature storage |
|---|---|---|
| Example 1 | 2034.3 | 86.5 |
| Example 2 | 2033.5 | 84.2 |
| Example 3 | 2030.2 | 93.0 |
| Example 4 | 2030.0 | 90.4 |
| Example 5 | 2025.2 | 96.3 |
| Example 6 | 2028.8 | 79.6 |
| Comparative Example 1 | 2046.3 | 56.8 |
| Comparative Example 2 | 1987.2 | 75.2 |
| Comparative Example 3 | 2021.4 | 68.4 |
| Comparative Example 4 | 2020.7 | 78.5 |
| Comparative Example 7 | 1007.4 | 84.1 |
| Comparative Example 8 | 1003.4 | 82.5 |

Referring to Table 3 above, it may be understood that the initial discharge capacities of the secondary batteries prepared in Examples 1 to 6 were increased compared to Comparative Examples 2 to 4, 7 and 8.

Since the secondary battery of Comparative Example 1 having a non-aqueous electrolyte solution without containing the first and second additives does not form a stable film compared to the secondary battery of Examples capable of forming a sufficient film as Li ions are easily consumed, the amount of the consumed Li ions is low during the evaluation of initial performance. Thus, it may be known that the initial discharge capacity was relatively increased compared to the secondary batteries of Examples 1 to 6.

Also, referring to Table 3 above, it may be understood that discharge capacity retention rates (%) of the secondary batteries prepared in Examples 1 to 5 were increased compared to Comparative Examples 1 to 4, 7 and 8.

It may be understood that the secondary battery prepared in Example 6 having a non-aqueous electrolyte solution containing the first additive and the second additive in the same amount exhibited a relatively decreased discharge capacity retention rate (%) after high temperature storage due to an increase in film resistance compared to those prepared in Examples 1 to 5.

Experimental Example 3. Volume Increase Rate Evaluation after High-Temperature Storage After each of the lithium secondary batteries prepared in Examples 1 to 6 and Comparative Examples 1 to 4 was charged at a rate of 0.33 C to 4.2 V under a constant current/constant voltage condition (0.05C cut) at room temperature (25° C.), each lithium secondary battery was insulated with an imide tape and an initial volume was then measured. The volume was calculated by measuring the weight in and out of deionized water based on Archimedes' principle.

Subsequently, after storage at 60° C. for 3 weeks, a thickness after high temperature storage of each lithium secondary battery was measured, and a volume increase rate was calculated by introducing the measured results to the following Equation 4 and the results thereof are presented in Table 4 below.

$$\text{Volume increase rate (\%)}=\{(\text{volume after high temperature storage}-\text{volume before high temperature storage})/\text{volume before high temperature storage}\}\times 100 \quad \text{[Equation 4]}$$

TABLE 4

| | Volume increase rate (%) after storage at 60° C. for 3 weeks relative to the initial volume |
|---|---|
| Example 1 | 2.9 |
| Example 2 | 3.3 |
| Example 3 | 2.0 |
| Example 4 | 2.3 |
| Example 5 | 1.3 |
| Example 6 | 3.1 |
| Comparative Example 1 | 10.0 |
| Comparative Example 2 | 4.6 |
| Comparative Example 3 | 6.3 |
| Comparative Example 4 | 4.6 |

Referring to Table 4 above, it may be understood that the volume increase rate (%) of the secondary batteries of Examples 1 to 6 of the present disclosure after high temperature storage at 60° C. was about 3.6% or less and thus the volume increase rate (%) after high-temperature storage thereof was increased in comparison to those of Comparative Examples 1 to 4.

The invention claimed is:

1. A lithium secondary battery comprising:

a negative electrode comprising a negative electrode active material, a positive electrode comprising a positive electrode active material represented by Formula 1, a separator disposed between the positive electrode and the negative electrode, and a non-aqueous electrolyte solution, wherein the non-aqueous electrolyte solution comprises a lithium salt, a non-aqueous organic solvent, a compound represented by Formula 2 as a first additive, and lithium difluorophosphate as a second additive:

$$Li_aNi_xCo_yM^1_zM^2_wO_2 \quad \text{[Formula 1]}$$

wherein, in Formula 1, $M^1$ is Mn, Al or a combination thereof, $M^2$ is at least one selected from the group consisting of Al, Zr, W, Ti, Ca and Sr, $0.8 \le a \le 1.2$, $0.7 \le x < 1$, $0 < y < 0.3$, $0 < z < 0.3$, and $0.01 < w \le 0.2$;

[Formula 2]

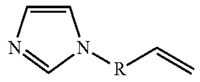

wherein, in Formula 2,

R is an alkylene group having 1 to 5 carbon atoms.

2. The lithium secondary battery as claimed in claim 1, wherein, in Formula 1, $M^2$ is one or more selected from the group consisting of Al, Zr, and Ti, $0.85 \le a \le 1.15$, $0.75 \le x \le 0.99$, $0.001 < y < 0.3$, $0.001 < z < 0.25$, and $0.01 < w \le 0.1$.

3. The lithium secondary battery as claimed in claim 1, wherein, in Formula 1, $M^2$ is Al, $0.9 \le a \le 1.05$, $0.8 \le x \le 0.95$, $0.01 < y < 0.25$, $0.01 \le z < 0.20$, and $0.01 < w \le 0.05$.

4. The lithium secondary battery as claimed in claim 1, wherein the positive electrode active material is $Li(Ni_{0.8}Co_{0.15}Al_{0.05})O_2$, $Li(Ni_{0.85}Mn_{0.08}Co_{0.05}Al_{0.02})O_2$, $Li(Ni_{0.86}Mn_{0.07}Co_{0.05}Al_{0.02})O_2$, $Li(Ni_{0.87}Mn_{0.07}Co_{0.04}Al_{0.02})O_2$, or $Li(Ni_{0.90}Mn_{0.03}Co_{0.05}Al_{0.02})O_2$.

5. The lithium secondary battery as claimed in claim 1, wherein, in Formula 2, R is an alkylene group having 1 to 3 carbon atoms.

6. The lithium secondary battery as claimed in claim 1, wherein the compound represented by Formula 2 is a compound represented by Formula 2a:

[Formula 2a]

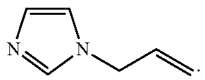

7. The lithium secondary battery as claimed in claim 1, wherein the compound represented by Formula 2 is included in an amount of 0.1 wt % to 5 wt % based on a total weight of the non-aqueous electrolyte solution.

8. The lithium secondary battery as claimed in claim 1, wherein a weight ratio of the compound represented by Formula 2 and the lithium difluorophosphate is 1:2 to 1:15.

9. The lithium secondary battery as claimed in claim 1, wherein a weight ratio of the compound represented by Formula 2 and the lithium difluorophosphate is 1:2 to 1:10.

10. The lithium secondary battery as claimed in claim 1, wherein the non-aqueous electrolyte solution comprises at least one of a cyclic carbonate-based organic solvent, a linear carbonate-based organic solvent, or a linear ester-based organic solvent, and further comprises at least one of a cyclic carbonate-based compound, a halogen-substituted carbonate-based compound, a sultone-based compound, a sulfate-based compound, a phosphate-based or phosphite-based compound, a borate-based compound, a benzene-based compound, an amine-based compound, an imidazole-based compound, a silane-based compound, or a lithium salt-based compound as a third additive.

11. The lithium secondary battery as claimed in claim 1, wherein the negative electrode active material comprises a silicon-based negative electrode active material and a carbon-based negative electrode active material in a weight ratio of 3:97 to 99:1.

12. The lithium secondary battery as claimed in claim 1, wherein the lithium salt comprises $LiPF_6$.

13. The lithium secondary battery as claimed in claim 10, wherein the third additive comprises at least one of vinylene carbonate, 1,3-propanesultone, ethylene sulfate, fluoroethylene carbonate (FEC), or $LiBF_4$.

* * * * *